United States Patent [19]

King et al.

[11] Patent Number: 4,826,839

[45] Date of Patent: May 2, 1989

[54] AZABICYCLIC BENZAMIDE DERIVATIVES

[75] Inventors: Francis D. King, Bishop's Stortford; Michael S. Hadley, Sawbridgeworth; Roger T. Martin, Stevenage, all of England

[73] Assignee: Beecham Group p.l.c., Brentford, England

[21] Appl. No.: 887,122

[22] Filed: Jul. 17, 1986

[30] Foreign Application Priority Data

Jul. 19, 1985 [GB] United Kingdom ............ 8518236

[51] Int. Cl.4 .............. A61K 31/535; A61K 31/54; C07D 498/08; C07D 513/03
[52] U.S. Cl. ........................... 514/214; 514/211; 514/221; 514/224.2; 514/230.5; 514/249; 540/552; 540/556; 540/579; 540/582; 544/47; 544/105; 544/349
[58] Field of Search .......... 540/552, 556, 579, 582; 544/47, 105; 514/214, 222, 228, 229, 232, 234, 236, 224.2, 230.5

[56] References Cited

U.S. PATENT DOCUMENTS

| | | | |
|---|---|---|---|
| 4,273,778 | 6/1981 | Hadley et al. | 424/265 |
| 4,346,089 | 8/1982 | Hadley et al. | 424/248.52 |
| 4,352,802 | 10/1982 | Blaney | 544/105 X |
| 4,612,319 | 9/1982 | King | 514/305 |

FOREIGN PATENT DOCUMENTS

| | | |
|---|---|---|
| 0013138 | 7/1980 | European Pat. Off. . |
| 0041817 | 12/1981 | European Pat. Off. . |
| 0094742 | 11/1983 | European Pat. Off. . |

Primary Examiner—Richard L. Raymond
Attorney, Agent, or Firm—James F. Haley, Jr.; David K. Barr; Doreen F. Shulman

[57] ABSTRACT

Compounds of formula (I) or a pharmaceutically acceptable salt thereof:

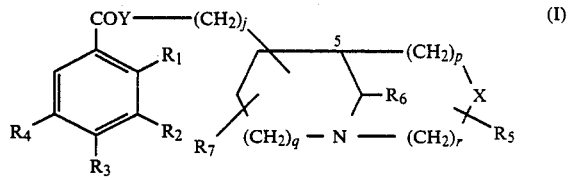

wherein:
j is 0 or 1;
q is 0, 1 or 2;
p is 0 and r is 2 or 3, or
p is 1 and r is 2;
X is O, S, SO or NR where R is hydrogen, $C_{1-6}$ alkyl or $C_{1-10}$ carboxylic acyl;
Y is NH; or O when $R_1$ is hydrogen; either $R_1$ is $C_{1-6}$ alkoxy and one of $R_2$, $R_3$ and $R_4$ is hydrogen and the other two are selected from hydrogen, halogen, $CF_3$, $C_{1-6}$ alkylthio, $C_{1-7}$ acyl, $C_{1-10}$ carboxylic acylamino, $C_{1-6}$ alkyl S(O) n wherein n is 0, 1 or 2, nitro or amino, aminocarbonyl or aminosulphonyl optionally substituted by one or two groups selected from $C_{1-6}$ alkyl, $C_{3-8}$ cycloalkyl, $C_{3-8}$ cycloalkyl $C_{1-4}$ alkyl or phenyl $C_{1-4}$ alkyl groups any of which phenyl moieties may be substituted by one or two groups selected from halogen, $CF_3$, $C_{1-6}$ alkyl or $C_{1-6}$ alkoxy; or $R_1$ is hydrogen and $R_2$, $R_3$ and $R_4$ are independently selected from hydrogen, $C_{1-6}$ alkyl, hydroxy, $C_{1-6}$ alkoxy, $C_{1-6}$ alkylthio or halo; or any two on adjacent carbon atoms together are $C_{1-2}$ alkylenedioxy and the third is hydrogen, $C_{1-6}$ alkyl, $C_{1-6}$ alkoxy or halo;
one of $R_5$ and $R_6$ is hydrogen, $C_{1-6}$ alkyl, phenyl or phenyl-$C_{1-6}$ alkyl, which phenyl moieties may be substituted by $C_{1-6}$ alkyl, $C_{1-6}$ alkoxy or halogen; and the other is hydrogen or $C_{1-6}$ alkyl; and
$R_7$ is hydrogen, $C_{1-6}$ alkyl, phenyl or phenyl-$C_{1-3}$ alkyl, which phenyl moieties may be substituted by $C_{1-6}$ alkyl, $C_{1-6}$ alkoxy, $CF_3$ or halogen having gastric motility enhancing activity, anti-emetic activity and/or 5-HT receptor antagonist activity, a process and intermediates for their preparation and their use as pharmaceuticals.

10 Claims, No Drawings

AZABICYCLIC BENZAMIDE DERIVATIVES

This invention relates to substituted benzamides and benzoates having pharmacological activity, to a process for their preparation and to their use as pharmaceuticals.

EP-A-94742 discloses a group of substituted azabicyclo compounds described as having dopamine antagonists useful in the treatment of disorders relating to impaired gastro-intestinal motility, emesis and/or disorders of the central nervous system.

A structurally distinct group of compounds has now been discovered which compounds have gastric motility enhancing activity, anti-emetic activity and/or 5-HT receptor antagonist activity.

Accordingly, the present invention provides a compound of formula (I) or a pharmaceutically acceptable salt thereof:

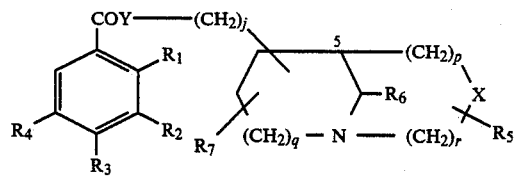

wherein:
j is 0 or 1;
q is 0, 1 or 2;
p is 0 and r is 2 or 3, or
p is 1 and r is 2;
X is O, S, SO or NR where R is hydrogen, $C_{1-6}$ alkyl or $C_{1-10}$ carboxylic acyl;
Y is NH; or O when $R_1$ is hydrogen; either $R_1$ is $C_{1-6}$ alkoxy and one of $R_2$, $R_3$ and $R_4$ is hydrogen and the other two are selected from hydrogen, halogen, $CF_3$, $C_{1-6}$ alkylthio, $C_{1-7}$ acyl, $C_{1-10}$ carboxylic acylamino, $C_{1-6}$ alkyl $S(O)n$ wherein n is 0, 1 or 2, nitro or amino, aminocarbonyl or aminosulphonyl optionally substituted by one or two groups selected from $C_{1-6}$ alkyl, $C_{3-8}$ cycloalkyl, $C_{3-8}$ cycloalkyl $C_{1-4}$ alkyl or phenyl $C_{1-4}$ alkyl groups any of which phenyl moieties may be substituted by one or two groups selected from halogen, $CF_3$, $C_{1-6}$ alkyl or $C_{1-6}$ alkoxy; or $R_1$ is hydrogen and $R_2$, $R_3$ and $R_4$ are independently selected from hydrogen, $C_{1-6}$ alkyl, hydroxy, $C_{1-6}$ alkoxy, $C_{1-6}$ alkylthio or halo; or any two on adjacent carbon atoms together are $C_{1-2}$ alkylenedioxy and the third is hydrogen, $C_{1-6}$ alkyl, $C_{1-6}$ alkoxy or halo;
one of $R_5$ and $R_6$ is hydrogen, $C_{1-6}$ alkyl, phenyl or phenyl-$C_{1-6}$ alkyl, which phenyl moieties may be substituted by $C_{1-6}$ alkyl, $C_{1-6}$ alkoxy or halogen; and the other is hydrogen or $C_{1-6}$ alkyl; and
$R_7$ is hydrogen, $C_{1-6}$ alkyl, phenyl or phenyl-$C_{1-3}$ alkyl, which phenyl moieties may be substituted by $C_{1-6}$ alkyl, $C_{1-6}$ alkoxy, $CF_3$ or halogen.

j is preferably 0; q is preferably 1; p is preferably 0; r is preferably 2.
X is often O.
Y is often NH.
Examples of $R_1$ when $C_{1-6}$ alkoxy include methoxy, ethoxy and n- and iso-propoxy. Preferably $R_1$ is a methoxy group.
Suitable examples of $R_3$ and $R_4$ include the following atoms and groups: hydrogen; chlorine, bromine; $CF_3$; methylthio, ethylthio, n and iso-propylthio; formyl, acetyl, propionyl, n- and iso-butyryl; formylamino, acetylamino, propionylamino, n- and iso-butyrylamino; methyl, ethyl and n- and iso-propylsulphone, -sulphinyl, -thia; nitro; methoxy, ethoxy and n- and iso-propoxy; hydroxy; amino, aminosulphonyl substituted by one or two methyl, ethyl, n- or iso-propyl groups, or by $C_3$, $C_4$ or $C_5$ cycloalkyl or by benzyl optionally substituted as defined above.

Particularly suitable $R_3$ and $R_4$ groups include hydrogen, halogen, and amino; and as "intermediates", acylamino and nitro, which can conveniently be converted to the corresponding amino groups.

Particularly preferred $R_3$ groups include 4-amino and 4-acylamino. Most preferably $R_3$ is 4-amino. Particularly preferred $R_4$ groups include 5-halo, such as 5-chloro.

In another group of compounds $R_3$ is hydrogen, 4-halo (e.g. chloro), or amino; and $R_4$ is 5-$C_{1-6}$ alkyl $S(O)_n$ (such as 5-methylsulphonyl, -sulphinyl or -thia) or 5-optionally alkylated aminosulphonyl.

When $R_1$ is hydrogen, examples of $R_2$ include halo, such as chloro and $C_{1-6}$ alkoxy, such as methoxy. Preferably $R_2$ is then chloro.

Examples of $R_3$ then include hydrogen, halo, such as chloro, hydroxy and $C_{1-6}$ alkoxy such as methoxy. Preferably $R_3$ is then hydrogen or chloro.

Examples or $R_4$ then include hydrogen, halo such as chloro and $C_{1-6}$ alkoxy, such as methoxy. Preferably $R_4$ is then hydrogen or chloro.

Suitable examples of $R_5$, $R_6$, and $R_7$ include hydrogen, methyl, ethyl, n- and iso-propyl, n-, iso-, sec- and tert-butyl; phenyl, phenylmethyl and phenylethyl, which phenyl moieties may be substituted by one or two methyl, ethyl, n- and iso-propyl, n-, iso-, sec- and tert-butyl; methoxy, ethoxy and n- and iso-propoxy; $CF_3$, fluoro, chloro or bromo.

Often $R_5$, $R_6$ and $R_7$ are hydrogen or methyl; preferably they are all hydrogen.

The pharmaceutically acceptable salts of the compounds of the formula (I) include acid addition salts with conventional acids such as hydrochloric, hydrobromic, boric, phosphoric, sulphuric acids and pharmaceutically acceptable organic acids such as acetic, tartaric, maleic, citric, succinic, benzoic, ascorbic, methanesulphonic, α-keto glutaric, α-glycerophosphoric, and glucose-1-phosphoric acids.

The pharmaceutically acceptable salts of the compounds of the formula (I) are usually acid addition salts with acids such as hydrochloric, hydrobromic, phosphoric, sulphuric, citric, tartaric, lactic and acetic acid.

Preferably the acid addition salt is the hydrochloride salt.

Pharmaceutically acceptable salts also include quaternary derivatives of the compounds of formula (I) such as the compounds quaternised by compounds $R_8$-Q wherein $R_8$ is $C_{1-6}$ alkyl, phenyl-$C_{1-6}$ alkyl or $C_{5-7}$ cycloalkyl, and Q is a radical corresponding to an anion of an acid. Suitable examples of $R_8$ include methyl, ethyl and n- and iso-propyl; and benzyl and phenethyl. Suitable examples of Q include halide such as chloride, bromide and iodide.

Examples of pharmaceutically acceptable salts also include internal salts such as pharmaceutically acceptable N-oxides.

The compounds of the formula (I), and their pharmaceutically acceptable salts (including quaternary derivatives and N-oxides) may also form pharmaceutically acceptable solvates, such as hydrates, and these are included wherever a compound of formula (I) or a salt is herein referred to.

It will of course be realised that some of the compounds of the formula (I) have at least one chiral centre (that numbered 5 in formula (I)) and thus are capable of existing in a number of stereoisomeric forms including enantiomers. The invention extends to each of these stereoisomeric forms (including enantiomers), and to mixtures thereof (including racemates). The different stereoisomeric forms may be separated one from the other by the usual methods, or any given isomer may be obtained by stereospecific or asymmetric synthesis.

There is a group of compounds within formula (I) of formula (II):

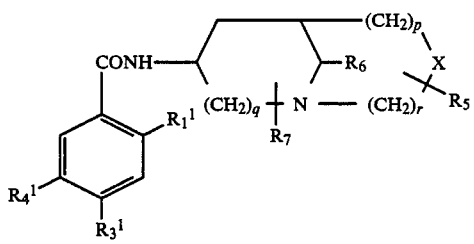

wherein $R_1^1$ is $C_{1-6}$ alkoxy;

$R_3^1$ is amino or $C_{1-7}$ alkanoylamino;

$R_4^1$ is halo or $C_{1-6}$ alkylthio;

and the remaining variables are as defined in formula (I). Suitable examples and preferred values for the variables are as described for the corresponding variables under formula (I).

There is a further group of compounds within formula (I) of formula (III):

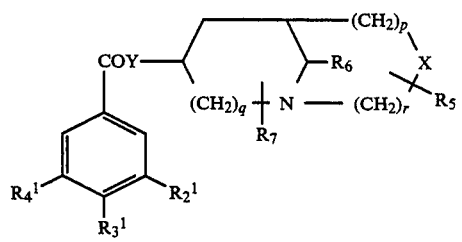

wherein $R_2^1$ is halo or $C_{1-6}$ alkoxy;

$R_3^1$ is hydrogen or $C_{1-7}$ alkoxy;

$R_4^1$ is halo or $C_{1-6}$ alkoxy; and the remaining variables are as defined in formula (I).

Suitable examples and preferred values for the variables are as described for the corresponding variables under formula (I).

The invention also provides a process for the preparation of a compound of formula (I), or a pharmaceutically acceptable salt thereof which process comprises reacting a compound of formula (IV):

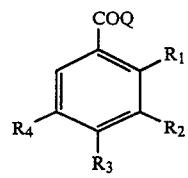

with a compound of formula (V):

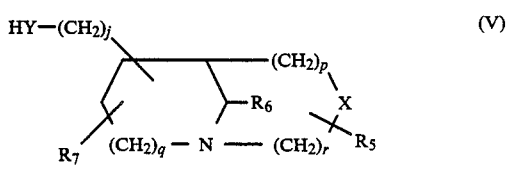

wherein Q is a leaving group and the remaining variables are as defined in formula (I); and thereafter optionally converting any $R_2$, $R_3$ or $R_4$ group to another $R_2$, $R_3$ or $R_4$ group respectively, and optionally forming a pharmaceutically acceptable salt of the resultant compound of formula (I).

Examples of groups Q displaceable by a nucleophile include halogen such as chloro and bromo, hydroxy, carboxylic acyloxy such as $C_{1-4}$ alkanoyloxy or $C_{1-4}$ alkoxycarbonyloxy and activated hydrocarbyloxy such as pentachlorophenoxy.

If a group Q is a halide, then the reaction is preferably carried out at non-extreme temperatures in an inert non-hydroxylic solvent, such as benzene, dichloromethane, toluene, diethyl ether, tetrahydrofuran (THF) or dimethylformamide (DMF). It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate. Temperatures of 0°–100° C., in particular 10°–80° C. are suitable.

If a group Q is hydroxy, then the reaction is generally carried out in an inert non-hydroxylic solvent, such as dichloromethane, THF or DMF optionally in the presence of a dehydrating catalyst, such as a carbodiimide, for example dicyclohexylcarbodiimide. The reaction may be carried out at any non-extreme temperature, such as -10° to 100° C., for example, 0° to 80° C. Generally, higher reaction temperatures are employed with less active compounds whereas lower temperatures are employed with the more active compounds.

If a group Q is carboxylic acyloxy, then the reaction is preferably carried in substantially the same manner as the reaction when Q is halide. Suitable examples of acyloxy leaving groups include $C_{1-4}$ alkanoyloxy and $C_{1-4}$ alkoxycarbonyloxy, in which case the reaction is preferably carried out in an inert solvent, such as methylene chloride, at a non-extreme temperature for example ambient temperatures in the presence of an acid acceptor, such as triethylamine. $C_{1-4}$ alkoxycarbonyloxy leaving groups may be generated in situ by treatment of the corresponding compound wherein Q is hydroxy with a $C_{1-4}$ alkyl chloroformate.

If a group Q is activated hydrocarbyloxy then the reaction is preferably carried out in an inert polar solvent, such as dimethylformamide. It is also preferred that the activated hydrocarbyloxy group is a pentachlorophenyl ester and that the reaction is carried out at ambient temperature.

When Y is O the compound of formula (V) is often in the form of a salt, such as the lithium salt.

Pharmaceutically acceptable salts of the compounds of this invention may be formed conventionally.

Acid addition salts may be formed for example by reaction of the base compound of formula (I) with a pharmaceutically acceptable organic or inorganic acid.

It will be apparent that compounds of the formula (I) containing an $R_2$, $R_3$ or $R_4$ group which is convertible to another $R_2$, $R_3$ or $R_4$ group are useful novel intermediates. A number of such conversions is possible not only for the end compounds of formula (I), but also for their intermediates as follows:

(i) a hydrogen substituent is convertible to a nitro substituent by nitration;

(ii) a nitro substituent is convertible to an amino substituent by reduction;

(iii) a $C_{1-7}$ acylamino substituent is convertible to an amino substituent by deacylation;

an amino substituent is convertible to a $C_{1-4}$ acylamino substituent by acylation with a carboxylic acid derivative;

(v) a hydrogen substituent is convertible to a halogen substituent by halogenation;

(vi) a $C_{1-6}$ alkylthio or $C_{1-6}$ alkylsulphinyl substituent is convertible to a $C_{1-6}$ alkylsulphinyl or a $C_{1-6}$ alkylsulphonyl substituent respectively by oxidation;

(vii) an amino, aminocarbonyl or aminosulphonyl, substituent is convertible to a corresponding substituent substituted by one or two groups as defined in formula (I), by N-alkylation;

(viii) an amino substituent is convertible to a $C_{1-6}$ alkylsulphonylamino group optionally N-substituted as defined by acylation with a $C_{1-6}$ alkylsulphonic acid.

Conversions (i) to (viii) are only exemplary and are not exhaustive of the possibilities.

In regard to (i), nitration is carried out in accordance with known procedures.

In regard to (ii), the reduction is carried out with a reagent suitable for reducing nitroanisole to aminoanisole.

In regard to (iii), deacylation is carried out by treatment with a base, such as an alkali metal hydroxide.

In regard to (iv) and (viii), the acylation is carried out with an acylating agent, such as the corresponding acid or acid chloride. Formylation is carried out with the free acid.

In regard to (v), halogenation is carried out with conventional halogenating agents.

In regard to (vi), oxidation is carried out at below ambient temperatures in a non-aqueous solvent, such as a chlorinated hydrocarbon, in the presence of an organic peracid, such as 3-chloroperbenzoic acid, or in water in the presence of a soluble strong inorganic oxidant, such as an alkali metal permanganate or in aqueous hydrogen peroxide. It will be realised that this process may also N-oxidise other N-moieties and suitable precautions will routinely be taken by the skilled man.

In regard to (vii), alkylation is carried out with a corresponding alkylating agent such as the chloride or bromide under conventional conditions.

Intermediates of the formula (IV) are known or can be prepared by analogous processes to those used for structurally similar known compounds.

Compounds of formula (V) are novel and form an aspect of the present invention. They may be prepared in accordance with the processes described in the descriptions hereinafter or by analogous methods thereto, such as those described in EP-A-94742 and (for formation of α and/or β isomers) in EP-13138.

The compounds of the present invention have gastric motility enhancing activity, anti-emetic activity and/or 5-HT antagonist activity. Compounds having gastric motility enhancing activity are useful in the treatment of disorders such as retarded gastric emptying, dyspepsia, flatulence, oesophagal reflux and peptic ulcer. Compounds having 5-HT antagonist activity are useful in the treatment of migraine, cluster headaches, trigeminal neuralgia, cytotoxic agent or radiation induced nausea and vomiting and/or cardiac arrhythmia. Examples of cytotoxic agents include cisplatin, doxorubicin and cyclophosphamide.

The compounds of formula (I) of particular interest for their gastric motility enhancing activity and anti-emetic activity are the compounds of formula (I) where $R_1$ is $C_{1-6}$ alkoxy.

The invention also provides a pharmaceutical composition comprising a compound of formula (I), or a pharmaceutically acceptable salt thereof and a pharmaceutically acceptable carrier.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art, for example with an enteric coating.

Suitable fillers for use include cellulose, mannitol, lactose and other similar agents. Suitable disintegrants include starch, polyvinylpolypyrrolidone and starch derivatives such as sodium starch glycollate. Suitable lubricants include, for example, magnesium stearate.

Suitable pharmaceutically acceptable wetting agents include sodium lauryl sulphate. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

The oral compositions may be prepared by conventional methods of blending, filling or tabletting. Repeated blending operations may be used to distribute the active agent throughout those compositions employing large quantities of fillers. Such operations are, of course, conventional in the art.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure of ethylene oxide before suspending in the sterile vehicle. Advantageously, a surfactant or wetting agent is included in the composition to facilitate uniform distribution of the compound of the invention.

The invention further provides a method of treatment or prophylaxis of disorders relating to impaired gastrointestinal motility; emesis; migraine, cluster headaches, trigeminal neuralgia, radiation or cytotoxic agent induced vomiting and/or cardiac arrhythmia in mammals, such as humans, which comprises the administration of an effective amount of a compound of the formula (I) or a pharmaceutically acceptable salt thereof, or a pharmaceutically acceptable solvate of either of the foregoing.

An amount effective to treat the disorders hereinbefore described depends on the relative efficacies of the compounds of the invention, the nature and severity of the disorder being treated and the weight of the mammal. However, a unit dose for a 70 kg adult will normally contain 0.05 to 500 mg for example 0.1 to 100 mg, of the compound of the invention. Unit doses may be administered once or more than once a day, for example, 2, 3 or 4 times a day, more usually 1 to 3 times a day, that is in the range of approximately 0.001 to 25 mg/kg/day, more usually 0.002 to 5 mg/kg/day.

No adverse toxicological effects are indicated at any of the aforementioned dosage ranges.

The invention also provides a compound of formula (I) or a pharmaceutically acceptable salt thereof for use as an active therapeutic substance, in particular for use in the treatment of disorders relating to impaired gastrointestinal motility; emesis; migraine, cluster headaches, trigeminal neuralgia, radiation or cytotoxic agent induced vomiting and/or cardiac arrhythmia.

The following Examples illustrate the preparation of compounds of formula (I); the following Descriptions illustrate the preparation of intermediates.

Abbreviations are as follows:

| Room Temperature | R.T. |
| Dimethylformamide | DMF |
| 1,2-Dimethoxyethane | DME |

Description 1

(±) 4-Benzyloxycarbonyl-2-morpholinomethanol (D1)

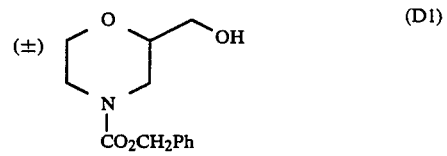

To 4-benzyl-2-morpholinomethanol (10.3 g) (F. Loftus, *Synthetic Commun.*, 1980, 10, 59), dissolved in ethanol (400 ml) was added conc. hydrochloric acid (7.5 ml) and the whole hydrogenated over 10% Pd/C (1.0 g) at atmospheric pressure until hydrogen uptake ceased. The catalyst was removed by filtration, washed with ethanol, and the filtrate treated with sodium hydroxide (4.3 g) dissolved in water (20 ml). The salts thus precipitated were removed by filtration and the filtrate evaporated under reduced pressure to give 2-morpholinomethanol (6.7 g) as an oil. This oil was dissolved in dry dichloromethane (100 ml) and triethylamine (8 ml), and cooled to ca. 0° C. under an atmosphere of nitrogen. Benzylchloroformate (8.0 ml), dissolved in dry dichloromethane (50 ml) was added dropwise to the stirred solution of the oil over a period of 15 min after which time the whole was left at R.T. for 1½ h. The solvent was then removed under reduced pressure and replaced by ether (200 ml). The organic phase was washed with 2N HCl (100 ml), sat. aq. NaHCO$_3$ (100 ml) and brine (100 ml) and then dried (Na$_2$SO$_4$). The solvent was removed under reduced pressure to give the title compound D1 (12.21 g, 91%) as an oil.

n.m.r. (CDCl$_3$)

| δ | 2.30–4.10 | (m, 10H) |
| | 5.00 | (s, 2H) |
| | 7.20 | (s, 5H) |

DESCRIPTION 2

Methyl-4-benzyloxycarbonyl-2-morpholinocarboxylate (D1)

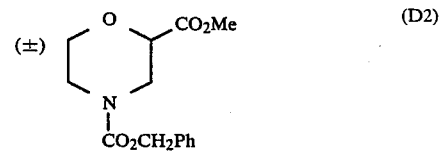

To a stirred suspension of the alcohol D1 (6.5 g) in water (45 ml) containing potassium hydroxide (1.75 g) was added solid potassium permanganate (6.25 g) portionwise over a period of 2 h. The whole was then stirred at R.T. for 18 h after which the solids were removed by filtration. The aqueous phase was washed with ether (1 × 100 ml), acidified with conc. hydrochloric acid and extracted with dichloromethane (3 × 80 ml). The organic phase was dried (Na$_2$SO$_4$) and the solvent removed under reduced pressure to give 4-benzyloxycarbonyl-2-morpholinocarboxylic acid (5.11 g) as a viscous oil. This oil was dissolved in dry dichloromethane (50 ml) and oxalyl chloride (1.8 ml) followed by DMF (ca. 3 drops) added. After stirring at R.T. for 45 min, methanol (20 ml) and triethylamine (6 ml) were added dropwise over 5 min with external cooling. The whole was then left at R.T. for 1½ h after which the solvent was removed under reduced pressure and replaced by ether (200 ml). The organic phase was washed with 2N HCl (50 ml), sat. aq. NaHCO$_3$ (50 ml), brine (50 ml) and then dried (Na$_2$SO$_4$). Evaporation of the solvent under reduced pressure gave the title compound D2 (4.57 g, 64%) as an oil.

n.m.r. (CDCl$_3$)

| δ | 2.80–4.30 | (m, 7H) |
|---|---|---|
| | 3.65 | (s, 3H) |
| | 5.08 | (s, 2H) |
| | 7.27 | (s, 5H) |

DESCRIPTION 3

(±) Methyl-2-morpholinocarboxylate (D3)

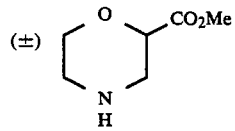

(D3)

To a stirred suspension of 10% Pd/C (1 g) in methanol (25 ml), under an atmosphere of nitrogen, was added cyclohexene (10 ml) and the carbamate D2 (4.57 g), dissolved in methanol (25 ml). The whole was then heated under reflux for 45 min before being allowed to cool to R.T. The solids were removed by filtration and the filtrate evaporated under reduced pressure to give the title compound D3 (2.23 g, 94%) as an oil.

n.m.r. (CDCl$_3$)

| δ | 1.90–4.30 | (m, 8H) |
|---|---|---|
| | 3.70 | (s, 3H) |

DESCRIPTION 4

(±) Methyl-4-(β-methoxycarbonylethyl)-2-morpholinocarboxylate (D4)

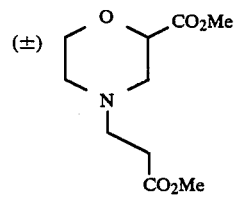

(D4)

To the amino-ester D3 (12.1 g) was added methyl acrylate (15 ml) and the whole heated under gentle reflux for 18 h. After cooling the reaction mixture to R.T., ether (200 ml) was added and the diester D4 extracted into 2N HCl (2×30 ml). The aqueous phase was then basified by the addition of solid potassium carbonate and extracted with dichloromethane (3×80 ml). The organic phase was dried (K$_2$CO$_3$) and evaporated under reduced pressure to give the title compound D4 (16.6 g, 82%) as an oil.

n.m.r. (CDCl$_3$)

| δ | 1.75–3.00 | (m, 8H) |
|---|---|---|
| | 3.10–4.20 | (m, 3H) |
| | 3.40 | (s, 3H) |
| | 3.50 | (s, 3H) |

The amino-ester D13, preparation described in Description 13 (Method I) and in Description 17 (Method II) may also be used in place of D3 in this procedure for the preparation of D4.

DESCRIPTION 5

(±)4-Oxa-1-azabicyclo[3.3.1]nonan-6-one (D5)

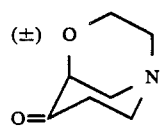

(D5)

A solution of the diester D4 (15.2 g) in dry toluene (1.5l) was added dropwise, over a period of 5 h, to a stirred suspension of potassium t-butoxide (21.3 g) in dry toluene (700 ml), heated to a gentle reflux under an atmosphere of nitrogen. After being heated to reflux for an additional 1 h, the reaction mixture was allowed to cool to R.T. and the product extracted into 5N HCl (2×100 ml). The aqueous phase was then heated under reflux for 18 h before being cooled to R.T. and made basic, then saturated, with solid potassium carbonate. The aqueous phase was extracted with dichloromethane (3×150 ml) and the organic phase dried (K$_2$CO$_3$). Evaporation under reduced pressure gave the title compound D5 (4.9 g, 56%) as an oil.

n.m.r. (CDCl$_3$)
δ2.00–4.10 (m, 11H)
i.r. νmax 1, 710 (C=0)cm$^{-1}$

DESCRIPTION 6

(±)4-Oxa-1-azabicyclo[3.3.1]nonan-6-one oxime hydrochloride (D6)

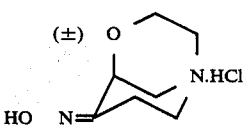

(D6)

To a solution of the ketone D5 (5.28 g) in ethanol (60 ml) was added hydroxylamine hydrochloride (4.31 g) and the whole heated under gentle reflux for 2 h. After cooling the reaction mixture to R.T., the solid was collected by filtration, washed with ethanol (10 ml) and dried in vacuo to give the title compound D6 (5.5 g, 93%). m.p. 259°–60° (ethanol) (D$_6$DMSO)

| δ 2.76–2.96 (m, 1H) |
|---|
| 3.04–3.21 (m, 1H) |
| 3.22–3.62 (m, 6H) |
| 3.77–3.93 (m, 1H) |
| 3.94–4.09 (m, 1H) |
| 4.38–4.46 (m, 1H) |
| 11.29,11.48 (2s, 1H) |

-continued 11.70–12.20 (m, 1H)

Description 7

(±)6α-Amino-4-oxa-1-azabicyclo[3.3.1]nonane (D7)

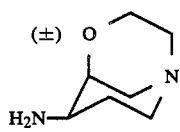
(D7)

To a stirred suspension of LiAlH$_4$ (1.5 g) in dry THF (30 ml) at 0° and under an atmosphere of nitrogen, was added conc. H$_2$SO$_4$ (1 ml) dropwise over a period of 1 min. After stirring at 0° for an additional 1 h, a solution of the oxime D6 (2.1 g [as its free base]) in dry THF (100 ml) was added dropwise over a period of 30 min. The whole was then heated under reflux for 2½ h before being cooled to R.T. and treated sequentually with water (1.5 ml), 2.5N NaOH (2.2 ml) and water (3.75 ml). The solids were then removed by filtration, washed with THF (100 ml) and the filtrate evaporated under reduced pressure to give the title compound D7 (1.78 g, 98%) as an oil.

DESCRIPTION 8

(±) 2-Cyanothiomorpholine (D8)

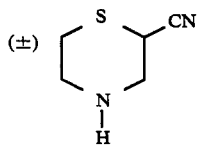
(D8)

A solution of cystamine (7.4 g) and α-chloroacrylonitrile (8 ml) in DME (100 ml) was stirred at ambient temperatures overnight. Sodium borohydride (4 g) was then added and the reaction heated to reflux for 1 h. The reaction mixture was cooled, K$_2$CO$_3$ (7 g) added and then re-heated to reflux for a further 6 h. The cooled reaction mixture was carefully acidified with 5N HCl and the product extracted into CH$_2$Cl$_2$ (3×200 ml). The residue obtained from evaporation of the solvent was heated to reflux with an excess of trifluoroacetic acid in EtOH (100 ml) for 12 h. The ethanol was removed and the residue partitioned between CH$_2$Cl$_2$ (300 ml) and aqueous K$_2$CO$_3$ solution. The organic layer was separated, dried (K$_2$CO$_3$), evaporated and the residue distilled to give the title compound (0.8) (3.2 g) bp 88°–90°/0.2 mmHg.

m.s. Found M+128.0409 C$_5$H$_8$N$_2$S requires 128.0410.

DESCRIPTION 9

(±) Ethyl 4-(β-ethoxycarbonylethyl)-2-thiomorpholine carboxylate (D9)

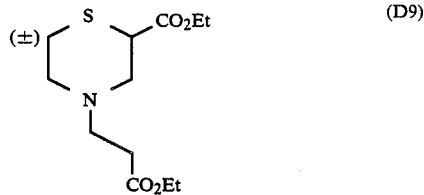
(D9)

A mixture of 2-cyanomorpholine (0.8) (3.2 g) and ethyl acrylate (4 ml) was stirred at ambient temperatures for 3 days. A solution of 30 ml of c.H$_2$SO$_4$ in EtOH (60 ml) was added and the mixture heated to reflux for 6 h. The reaction mixture was cooled, ice/water (100 ml) was added and the aqueous solution washed with Et$_2$O (2×200 ml). The aqueous layer was then basified with K$_2$CO$_3$ solution and the product extracted into Et$_2$O (3×100 ml). Evaporation of the solvent afforded the title compound D9 (4.9 g) which was used without further purification.

DESCRIPTION 10

(±) 4-Thia-1-azabicyclo[3,3,1]nonan-6-one (D10)

(D10)

Following the procedures outlined in Description 5, D9 (4.1 g) was converted to the title compound D10 (1.1 g) m.s. Found M+157.0563; C$_{17}$H$_{11}$NOS requires 157.0565.

DESCRIPTION 11 (±)

6α-Amino-4-thia-1-azabicyclo[3,3,1]nonane (D11)

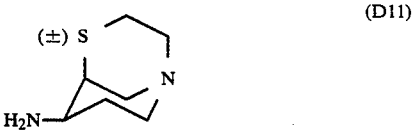
(D11)

Following the procedures outlined in Descriptions (6) and (7); D10 (1.1 g) was converted to the title compound (D11) (0.63 g).

DESCRIPTION 12

(±) 2-Cyanomorpholine (D12)

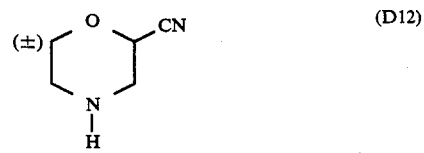
(D12)

A solution of ethanolamine (3ml) and 2-chloroacrylonitrile (4 ml) in DME (50 ml) was stirred initially at 0° for 1 h, then R.T. for 1 h. The reaction mixture was then re-cooled to 0° C. and solid potassium t-butoxide (6.0 g) was added in one portion. After stirring to R.T. overnight, the reaction was heated to reflux for 1 h, cooled and treated with saturated NaHCO3 solution (20 ml). Solid K2C3 was then added to saturation and the product extracted into Et2O (3×100 ml). The extracts were dried (K2CO3) and distilled to give the title compound D12 (2.6 g) b.p. 80°/3 mm Hg.

| $^1$H-nmr(CDCl$_3$)δ | 4.56 | (t, 1H) |
|---|---|---|
| | 3.93 | (dt, 1H) |
| | 3.72 | (dt, 1H) |
| | 3.17 | (dd, 1H) |
| | 3.06 | (dd, 1H) |
| | 2.96–2.86 | (m, 2H) |
| | 1.85 | (brs, 1H) |

$^{13}$C-nmr (ppm, CDCl$_3$) 117.3, 65.6, 64.7, 48.3, 45.1

DESCRIPTION 13

(±) Ethyl 2-morpholinocarboxylate (D13)(Method I)

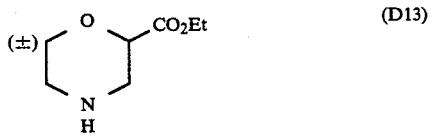

A solution of 2-cyanomorpholine (D.12) (2.6 g) in ethanol (50 ml) and conc. H$_2$SO$_4$ (10 ml) was heated under reflux for 48 h. The reaction mixture was cooled and carefully neutralised with aqueous K$_2$CO$_3$ solution. Extraction with ethyl acetate (3×100 ml), drying of the extracts (K$_2$CO$_2$) and evaporation afforded the title compound D13 (3.5 g).

| $^1$H-nmr(CDCl$_3$)δ | 4.27 | (q, 2H) |
|---|---|---|
| | 4.30–3.40 | (m, 3H) |
| | 3.20–2.70 | (m, 4H) |
| | 1.97 | (s, 1H) |
| | 1.33 | (t, 3H) |

DESCRIPTION 14

(±) Ethyl 4-(β-ethoxycarbonylethyl)-2-morpholinocarboxylate (D14)

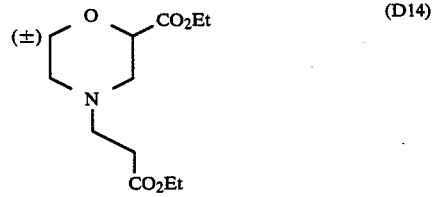

Following the procedure outlined in Description 4, (±)ethyl-2-morpholinocarboxylate (D13) and ethyl acrylate were reacted to give the title compound (D14)

| $^1$H-nmr(CDCl$_3$)δ | 4.5 –3.3 | (m, 7H) |
|---|---|---|
| | 3.0 –2.0 | (m, 8H) |
| | 1.27 | (t, 3H) |
| | 1.23 | (t, 3H) |

DESCRIPTION 15

(±) 4-Benzyl-2-cyanomorpholine (D15)

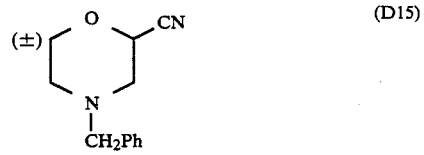

A solution of N-benzyl ethanolamine (14.2 ml) and 2-chloroacrylonitrile (8 ml) in Et$_2$O (100 ml) was stirred at r.t. for 5 days. The Et$_2$O was removed in vacuo and DME (300 ml) added. The stirred solution was cooled to 0° and potassium t-butoxide (12 g) was added and the whole stirred at 0° C. for 2 h, then heated under reflux for 1 h. Saturated NaHCO$_3$ solution (100 ml) was added and the product extracted into Et$_2$O (3×100 ml). The organic extracts were dried (K$_2$CO$_3$), evaporated and distilled to give the title compound (D15) (16.4 g). b.p. 125°–35°/0.2 mm Hg.

| $^1$H-nmr(CDCl$_3$)δ | 7.20 | (s, 5H) |
|---|---|---|
| | 4.47 | (t, 1H) |
| | 4.20–3.07 | (m, 2H) |
| | 3.45 | (s, 2H) |
| | 2.90–2.20 | (m, 4H) |

Description 16

(±) Ethyl 4-benzyl-2-morpholinocarboxylate (D16)

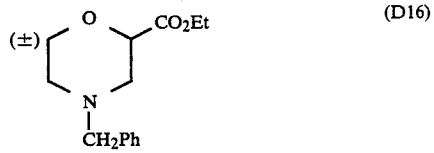

A solution of (±) 4-benzyl-2-cyanomorpholine (D15) (16.4 g) in EtOH (150 ml) and conc. H$_2$SO$_4$ (24 ml) was heated under reflux for 48 h. The solution was cooled and concentrated in vacuo to ca. half the above volume, basified with aqueous K$_2$CO$_3$ solution and the product extracted into Et$_2$O (3×100 ml). The organic extracts were dried (K$_2$CO$_3$) and evaporated to yield the title compound (D 16) (15.9 g).

| $^1$H-nmr(CDCl$_3$)δ | 7.20 | (s, 5H) |
|---|---|---|
| | 4.40–3.60 | (m, 5H including 4.13, q, 2H) |
| | 3.47 | (s, 2H) |
| | 3.10–2.00 | (m, 4H) |
| | 1.23 | (t, 3H) |

Description 17

(±) Ethyl 2-morpholinocarboxylate (D13) Method II

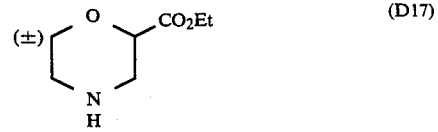

A solution of (±) ethyl 4-benzyl-2-morpholinocarboxylate (D16) (15.9 g) and trifluoroacetic acid (5.5 ml) in EtOH (200 ml) was hydrogenated over 10% Pd-charcoal (0.5 g) until the theoretical volume of hydrogen had been absorbed. The catalyst was removed by filtration and the solution concentrated in vacuo. The residue was diluted with water (10 ml) then neutralised and saturated with solid $K_2CO_3$. Extraction with EtOAc (3×100 ml) gave the title compound (D13) (8.9 g) identical to that described in Description 13.

EXAMPLE 1

(±) 4-Acetamido-5-chloro-2-methoxy-N-(6'α-[4'-oxa-1'azabicyclo[3,3,1[nonyl])benzamide hydrochloride (E1)

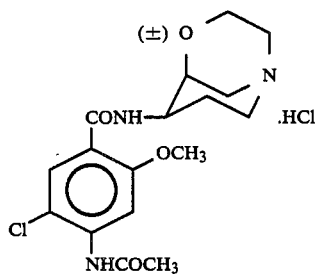

To a stirred solution of 4-acetamido-5-chloro-2-methoxybenzoyl chloride (3.4 g) in dry toluene (200 ml) was added a solution of D7 (1.78 g) in dry toluene (100 ml) over a period of 15 min. The whole was then stirred at R.T. for an additional 1½ h. before the precipitate was collected by filtration and dried in vacuo to give the title compound E1 (4.66 g).

Example 2

(±) 4-Amino-5-chloro-2-methoxy-N-(6'α-[4'-oxa-1'azabicyclo [3,3,1]nonyl])benzamide (E2)

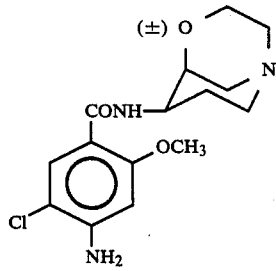

To a solution of E1 (4.66 g) in ethanol (100 ml) was added 2.5N NaOH (20 ml) and water (20 ml), and the whole heated on a steam bath for 1½ h. The reaction mixture was cooled to R.T. and the solvent removed under reduced pressure The residue was then partitioned between dichloromethane (100 ml) and saturated aqueous potassium carbamate (15 ml) and the aqueous phase was further extracted with dichloromethane (2×50 ml). The combined organic extracts were dried ($K_2CO_3$) and evaporated under reduced pressure to give a crude solid (1.35 g). Recrystallisation from methanol-ethyl acetate gave the title compound E2 (0.40 g, 10%) m.p. 224°–224.5°.

n.m.r. (CDCl$_3$)

| δ | | |
|---|---|---|
| | 1.85–2.07 | (m, 1H) |
| | 2.08–2.22 | (m, 1H) |
| | 2.70–3.23 | (m, 6H) |
| | 3.30–3.53 | (m, 2H) |
| | 3.60–3.85 | (m, 2H) |
| | 3.90 | (s, 3H) |
| | 3.90–4.08 | (m, 1H) |
| | 4.10–4.30 | (m, 1H) |
| | 6.32 | (s, 1H) |
| | 8.04 | (s, 1H) |
| | 8.22–8.40 | (m, 1H) |

EXAMPLE 3

(±) 4-Acetamido-5-chloro-2-methoxy-N-(6'α-[4'-thia-1'-azabicyclo[3,3,1]nonyl])benzamide (E3)

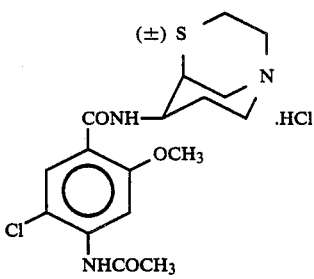

Following the procedures outlined in Example 1; D11 (0.6 g) was converted to the title compound E3 (0.8 g), isolated as the free base.

EXAMPLE 4

(±)4-Amino-5-chloro-2-methoxy-N-(6'α-[4'-thia-1'-azabicyclo[3,3,1 ]nonyl])benzamide (E4)

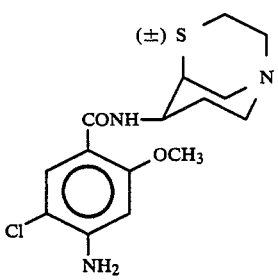

Following the procedures outlined in Example 2, E3 (0.8 g) was converted to the title compound E4 (0.6 g) m.p. 234°–6° C.

n.m.r. (CDCl$_3$; 270 MHz)

| δ | | |
|---|---|---|
| | 1.75–1.95 | (m, 1H) |
| | 1.98 –2.10 | (m, 1H) |
| | 2.15 –2.28 | (m, 1H) |
| | 2.50 | (brs, 1H) |
| | 3.05 –3.65 | (m, 7H) |
| | 3.97 | (s, 3H) |
| | 4.41 | (brs, 2H) |
| | 4.52–4.65 | (m, 1H) |
| | 6.30 | (s, 1H) |
| | 8.10 | (s, 1H) |
| | 8.52 | (d, 1H) |

PHARMACOLOGICAL DATA

1. Intragastric pressure in the rat

Intragastric pressure changes were recorded from fasted conscious and restrained rats using a saline filled catheter inserted into the lumen of the stomach via a permanent gastric fistula. The catheter was connected to a physiological pressure transducer and pressure changes recorded on a hot wire pen recorder. An index of activity was obtained by measuring the average height of pressure waves during 10 minute periods. Values for 4 such periods were obtained during assessment of spontaneous activity prior to dosing and for the 40 minute period following dosing with compound or vehicle. The Student's "t" test was applied to the mean values obtained for activity prior to and post treatment. Groups of 10 animals were used for each treatment.

The compound of Example 2 had an $ED_{50}$ of 0.1 mg/kg s.c.

2. Intraluminal pressure in the Heidenhain pouch of the dog

Pressure changes were recorded via a saline filled catheter inserted, with airtight closure, into the fistula of a chronic Heidenhain pouch of the previously fasted and lightly restrained conscious dog. The catheter was connected to a physiological pressure transducer and pressure changes recorded on a hot wire pen recorder. Compounds were administered when the motility was in a phase of relatively low activity and the dose range determined which induced an increase in the amplitude of rhythmical contractions for a period of at least 4–5 minutes.

The compound of Example 2 and 4 were active at a dose of 0.01 mg/kg s.c.

We claim:

1. A compound of the formula (I) or a pharmaceutically acceptable salt thereof:

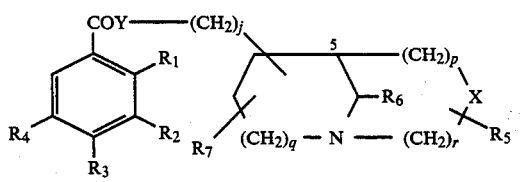

wherein:
j is 0 or 1;
q is 0, 1 or 2;
p is 0 and r is 2;
X is O, S or SO;
Y is NH; or O when $R_1$ is hydrogen; either $R_1$ is $C_{1-6}$ alkoxy and one of $R_2$, $R_3$ and $R_4$ is hydrogen and the other two are selected from hydrogen, halogen, $CF_3$, $C_{1-6}$ alkylthio, $C_{1-7}$ acyl, $C_{1-10}$ carboxylic acylamino, $C_{1-6}$ alkyl S(O)n wherein n is 0, 1 or 2, nitro or amino, aminocarbonyl or aminosulphonyl optionally substituted by one or two groups selected from $C_{1-6}$ alkyl, $C_{3-8}$ cycloalkyl, $C_{3-8}$ cycloalkyl $C_{1-4}$ alkyl or phenyl $C_{1-4}$ alkyl groups any of which phenyl moieties may be substituted by one or two groups selected from halogen, $CF_3$, $C_{1-6}$ alkyl or $C_{1-6}$ alkoxy; or $R_1$ is hydrogen and $R_2$, $R_3$ and $R_4$ are independently selected from hydrogen, $C_{1-6}$ alkyl, hydroxy, $C_{1-6}$ alkoxy, $C_{1-6}$ alkylthio or halo; or any two on adjacent carbon atoms together are $C_{1-2}$ alkylenedioxy and the third is hydrogen, $C_{1-6}$ alkyl, $C_{1-6}$ alkoxy or halo;

one of $R_5$ and $R_6$ is hydrogen, $C_{1-6}$ alkyl, phenyl or phenyl $C_{1-6}$ alkyl, which phenyl moieties may be substituted by $C_{1-6}$ alkyl, $C_{1-6}$ alkoxy or halogen; and the other is hydrogen or $C_{1-6}$ alkyl; and $R_7$ is hydrogen $C_{1-6}$ alkyl, phenyl or phenyl-$C_{1-3}$ alkyl, which phenyl moieties may be substituted by $C_{1-6}$ alkyl, $C_{1-6}$ alkoxy, $CF_3$ or halogen.

2. A compound according to claim 1 of formula (II):

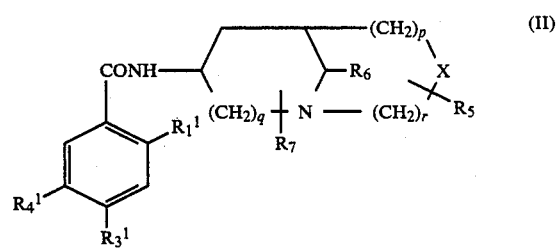

wherein $R_1{}^1$ is $C_{1-6}$ alkoxy;
$R_3{}^1$ is amino or $C_{1-7}$ alkanoylamino;
$R_4{}^1$ is halo or $C_{1-6}$ alkylthio;
and the remaining variables are as defined in claim 1.

3. A compound according to claim 2 wherein q is 1, p is 0 and r is 2.

4. A compound according to claim 2 wherein $R_1$ is methoxy.

5. A compound according to claim 2 wherein $R_4{}^1$ is chloro or bromo.

6. A compound according to claim 2 wherein $R_5$, $R_6$ and $R_7$ are all hydrogen.

7. (±)4-Amino-5-chloro-2-methoxy-N-(6'α-[4'-oxa-1'-azabicyclo[3,3,1]nonyl])benzamide or a pharmaceutically acceptable salt thereof.

8. (±)4-Amino-5-chloro-2-methoxy-N-(6'α-[4'-thia-1'-aza-bicyclo [3,3,1 ]nonyl])benzamide or a pharmaceutically acceptable salt thereof.

9. A pharmaceutical composition for the treatment of disorders associated with impaired gastro-intestinal motility or emesis comprising an effective amount of a compound of formula (I) according to claim 2 or a pharmaceutically acceptable salt thereof, and a pharmaceutically acceptable carrier.

10. A method of treatment of disorders associated with impaired gastro-intestinal motility in mammals, which comprises the administration of an effective amount of a compound according to claim 2 or a pharmaceutically acceptable salt thereof.

* * * * *